United States Patent
Möckli

(10) Patent No.: US 6,762,287 B2
(45) Date of Patent: Jul. 13, 2004

(54) CATIONIC IMIDAZOLE AZO DYES

(75) Inventor: Peter Möckli, Schönenbuch (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/398,823

(22) PCT Filed: Oct. 10, 2001

(86) PCT No.: PCT/EP01/11708

§ 371 (c)(1), (2), (4) Date: Apr. 10, 2003

(87) PCT Pub. No.: WO02/31056

PCT Pub. Date: Apr. 18, 2002

(65) Prior Publication Data

US 2004/0049020 A1 Mar. 11, 2004

(30) Foreign Application Priority Data

Oct. 12, 2000 (CH) ............................................. 2006/00

(51) Int. Cl.⁷ ........................... C09B 44/16; D06P 3/32; D21H 21/28
(52) U.S. Cl. ............................ 534/607; 534/608; 8/655
(58) Field of Search ................................ 534/607, 608; 8/655

(56) References Cited

U.S. PATENT DOCUMENTS

| | | | |
|---|---|---|---|
| 3,102,879 A | * 9/1963 | Baumann et al. | ............ 534/607 |
| 3,173,907 A | * 3/1965 | Klingsberg et al. | .......... 534/607 |
| 4,341,853 A | 7/1982 | Horie et al. | ................... 430/83 |
| 4,687,842 A | * 8/1987 | Henzi | .......................... 534/607 |
| 5,708,151 A | * 1/1998 | Mockli | ........................ 534/608 |

FOREIGN PATENT DOCUMENTS

| | | | |
|---|---|---|---|
| EP | 714954 | * | 6/1996 |
| FR | 1238315 | * | 8/1960 |
| FR | 79556 | * | 12/1962 |
| FR | 2393030 | * | 12/1978 |

OTHER PUBLICATIONS

Deligeorgiev et al.,Dyes and Pigments, 31(3), 219–224, 1996.*
Baumann et al., Chemical Abstracts, 60:10828h, "New Synthesis of Diazastyryl Dyes",1964.*

* cited by examiner

Primary Examiner—Fiona T. Powers
(74) Attorney, Agent, or Firm—Kevin T. Mansfield

(57) ABSTRACT

Dyes of formula (1) or (2) wherein $R_1$, $R_1'$, $R_2$ and $R_2'$ are each independently of the others hydrogen, $C_1$–$C_4$alkyl, halogen or nitro, $R_3$, $R_3'$, $R_4$ and $R_4'$ are each independently of the others $C_1$–$C_4$alkyl unsubstituted or substituted by OH, $C_1$–$C_4$alkoxy, halogen, CN or phenyl, $R_5$ is hydrogen or $C_1$–$C_4$alkyl, $R_6$ is unsubstituted or amino-substituted $C_5$–$C_{12}$alkyl; or unsubstituted or amino-substituted $C_5$–$C_8$cycloalkyl; or phenyl-substituted $C_1$–$C_4$alkyl; or wherein $R_5$ and $R_6$ together with the nitrogen atom linking them from a piperazine ring, which is substituted, at the nitrogen atom that is not bonded to the phenyl group, by $C_1$–$C_4$-alkyl or phenyl, the alkyl and phenyl radicals mentioned as substituents of the nitrogen atom of the piperazine ring being unsubstituted or substituted by amino, $X_1$, $X_2$, $X_3$ and $X_4$ are each independently of the others hydrogen, $C_1$–$C_4$alkyl, $C_1$–$C_4$alkoxy or halogen, $Y_1$ is a bridging member of formula (I) or —NH—$(CH_2)_6$—NH—, and $X^-$ is an anion, as wels as methods of dyeing or printing textile materials, leather, paper or glass fibres with those dyes, are described.

15 Claims, No Drawings

CATIONIC IMIDAZOLE AZO DYES

The present invention relates to novel cationic imidazole azo dyes, to processes for their preparation and to their use for dyeing textile materials, leather, paper or glass fibres.

The novel imidazole azo dyes correspond to formula

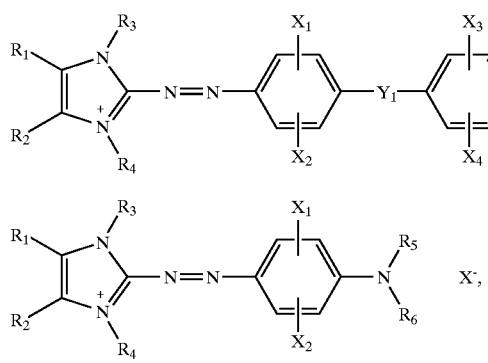

(1)

(2)

wherein $R_1$, $R_1'$, $R_2$ and $R_2'$ are each independently of the others hydrogen, $C_1$–$C_4$alkyl, halogen or nitro, $R_3$, $R_3'$, $R_4$ and $R_4'$ are each independently of the others $C_1$–$C_4$alkyl unsubstituted or substituted by OH, $C_1$–$C_4$alkoxy, halogen, CN or phenyl, $R_5$ is hydrogen or $C_1$–$C_4$alkyl, $R_6$ is unsubstituted or amino-substituted $C_5$–$C_{12}$alkyl; or unsubstituted or amino-substituted $C_5$–$C_8$cycloalkyl; or phenyl-substituted $C_1$–$C_4$alkyl;

or wherein $R_5$ and $R_6$ together with the nitrogen atom linking them form a piperazine ring, which is substituted, at the nitrogen atom that is not bonded to the phenyl group, by $C_1$–$C_4$-alkyl or phenyl, the alkyl and phenyl radicals mentioned as substituents of the nitrogen atom of the piperazine ring being unsubstituted or substituted by amino, $X_1$, $X_2$, $X_3$ and $X_4$ are each independently of the others hydrogen, $C_1$–$C_4$alkyl, $C_1$–$C_4$alkoxy or halogen, $Y_1$ is a bridging member of formula

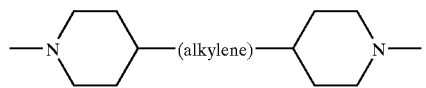

or —NH—$(CH_2)_6$—NH—, and $X^-$ is an anion.

The alkylene groups in the bridging member $Y_1$ may be straight-chain, branched or cyclic and may also be substituted, for example by halogen, alkoxy or hydroxy. In addition, they may be interrupted by hetero atoms, e.g. O or $NR_5$, wherein $R_5$ is hydrogen or $C_1$–$C_4$alkyl. Preference is given to a straight-chain or branched $C_1$–$C_{12}$alkylene radical. Special preference is given to $C_1$–$C_6$alkylene radicals, more especially $C_2$–$C_4$alkylene radicals. Propylene radicals, especially the 1,3-propylene radical, are of particular importance.

Suitable alkylene radicals are e.g. ethylene, 1,3-propylene, 1,2-propylene, 1,2-butylene, 1,4-butylene, 1,6-hexylene, 1,8-octylene, 1,12-dodecylene, 1,4-cyclohexylene, 2-hydroxy-1,3-propylene, 2-chloro-1,3-propylene and 3-oxa-1,5-pentylene.

According to the invention, alkyl radicals are to be understood as being generally straight-chain or branched alkyl radicals, e.g. methyl, ethyl, n- and iso-propyl and n-, sec- or tert-butyl.

Such alkyl radicals may, like the cycloalkyl groups, be mono- or poly-substituted, for example by hydroxy, carboxy, halogen, cyano, amino or $C_1$–$C_4$alkoxy.

The alkoxy radicals may have e.g. from 1 to 4 carbon atoms, for example methoxy, ethoxy, propoxy, isopropoxy, n-butoxy, isobutoxy and tert-butoxy. The alkoxy groups also may be substituted, e.g. by the radicals listed as possible substituents for alkyl groups, especially by hydroxy or $C_1$–$C_4$alkoxy.

Suitable anions $X^-$ include both inorganic and organic anions, for example halide, such as chloride, bromide or iodide, sulfate, hydrogen sulfate, methyl sulfate, boron tetrafluoride, aminosulfonate, perchlorate, carbonate, bicarbonate, phosphate, nitrate, benzenesulfonate, formate, acetate, propionate, lactate or complex anions, such as the anion of a zinc chloride double salt.

The anion is generally predetermined by the preparation process. Preferably, chlorides, hydrogen sulfates, sulfates, methosulfates, phosphates, formates, lactates or acetates are present. Highly preferred are chlorides.

Halogen is to be understood as being fluorine, bromine, iodine and especially chlorine.

$R_1$, $R_1'$, $R_2$ and $R_2'$ are preferably each methyl and especially each hydrogen.

$R_3$, $R_3'$, $R_4$ and $R_4'$ are preferably each ethyl, hydroxyethyl or especially methyl.

$X_1$, $X_2$, $X_3$ and $X_4$ are preferably each methoxy, methyl, chlorine or especially hydrogen.

$Y_1$ is preferably a bridging member of formula —NH—$(CH_2)_6$—NH—.

$R_5$ is preferably hydrogen, methyl or ethyl, especially hydrogen or methyl. Preferably, $R_5$ is hydrogen.

$C_5$–$C_{12}$Alkyl radicals $R_6$ are preferably corresponding unsubstituted or amino-substituted $C_5$–$C_8$alkyl radicals and preferably such $C_6$–$C_8$alkyl radicals.

$C_5$–$C_8$Cycloalkyl radicals $R_6$ are preferably corresponding unsubstituted or amino-substituted cyclohexyl radicals.

Phenyl-substituted $C_1$–$C_4$alkyl $R_6$ is preferably benzyl.

$R_6$ is especially preferably unsubstituted or amino-substituted $C_5$–$C_{12}$alkyl; or unsubstituted or amino-substituted $C_5$–$C_8$cycloalkyl; or phenyl-substituted $C_1$–$C_4$alkyl.

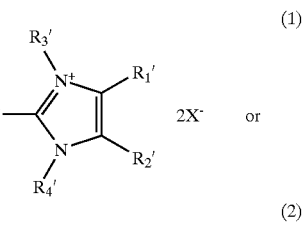

More preferably, $R_6$ is unsubstituted or amino-substituted $C_5$–$C_8$alkyl;

or unsubstituted or amino-substituted cyclohexyl;

or phenyl-substituted $C_1$–$C_4$alkyl.

Especially preferred dyes of formula (1) are those of formula

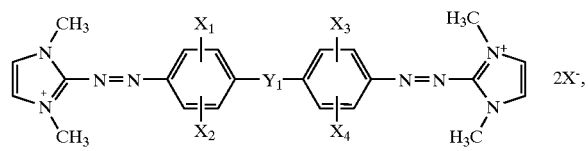

(1a)

wherein $X_1$, $X_2$, $X_3$ and $X_4$ are each independently of the others hydrogen, methyl or methoxy, especially hydrogen, $Y_1$ is as defined above under formula (1), especially a bridging member of formula —NH—$(CH_2)_6$—NH—, and $X^-$ is an anion. As to $X^-$ the preferences given above apply.

Especially preferred dyes of formula (2) are those of formula

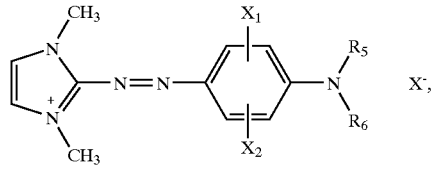

(2a)

wherein $X_1$ and $X_2$ are each independently of the others hydrogen, methyl or methoxy, especially hydrogen, and $R_5$, $R_6$ and $X^-$ are as defined above under formula (2). As to $R_5$, $R_6$ and $X^-$ the abo preferences apply.

Preferably, in formula (2a) $R_5$ is hydrogen.

Preferably, in formula (2a) $R_6$ is unsubstituted or amino-substituted $C_5$–$C_{12}$alkyl;

or unsubstituted or amino-substituted $C_5$–$C_8$cycloalkyl;

or phenyl-substituted $C_1$–$C_4$alkyl.

The dyes of formulae (1) and (2) can be prepared according to methods known per se (see e.g. EP-A-714 954).

The dyes of formula (1) can be obtained, for example, by reacting a compound of formula

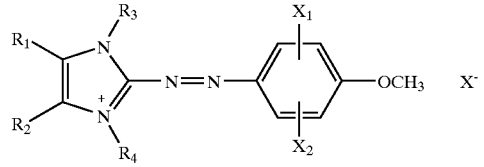

(3)

with a diamine of formula

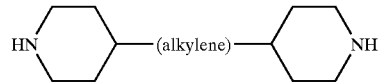

(4a)

or

(4b)

wherein the substituents have the definitions and preferred meanings indicated above. Alternatively, it is also possible to use as compounds of formula (3) those compounds which, instead of the methoxy group indicated, contain halogen, e.g. chlorine, or $C_2$–$C_4$alkoxy. The compounds of formulae (3), (4a) and (4b) are known or can be prepared in a manner known per se. For example, the compounds of formula (3) can be obtained by diazotising 4-alkoxyanilines, coupling the product with an imidazole and then carrying out alkylation and quaternisation.

The reaction of a compound of formula (3) with a diamine of formula (4a) or (4b) can be carried out, for example, at a temperature of about from 40 to 100° C., preferably from 40 to 70° C., optionally under pressure and/or in an inert gas atmosphere, and in an inert solvent, e.g. in water or aliphatic alcohols, e.g. $C_1$–$C_8$alcohols, such as methanol, ethanol or especially isopropanol, but more especially in aprotic polar solvents, such as dimethylformamide or dimethyl sulfoxide. In the case of diamines that are liquid under the reaction conditions, it is possible, if desired, to dispense with a solvent.

The dyes of formula (2) can be obtained, for example, in a similar way as given above for the preparation of the compounds of formula (1). However, instead of the diamines of formulae (4a) and (4b) an amine of formula $HN(R_5)R_6$ is used.

The dyes of formulae (1) and (2) according to the invention are suitable for dyeing polyacrylonitrile materials and leather, but especially for dyeing paper, since they possess a high substantivity for that substrate. The dyes give dyeings in red shades. The resulting dyeings are distinguished by good fastness properties. The effluents are in most cases completely colourless.

The dyes of formula (1) or (2) may also be used in mixtures with other cationic dyes. Especially preferred dye mixtures are those which contain a dye of formula (1) or a dye of formula (2) and a cationic copper phthalocyanine dye. Using such mixtures there are obtained on paper dyeings in highly attractive neutral shades. Suitable copper phthalocyanine dyes are those dyes which are known from the literature and can be used for the dyeing of paper, especially the dyes described in EP-A-0 184 991, DE-A-3 111 199 and EP-A-0 174 586.

The dyes of formula (1) or (2) can be formulated as a solid or liquid commercial form and employed for the dyeing of paper.

In the form of powder or granules, the dyes are used especially in discontinuous mass dyeing, in which the dye is added in batches to the pulper, hollander or mixing vat. In this case the dyes are preferably used in the form of dye preparations which may comprise diluents, e.g. urea as solubiliser, dextrins, Glauber's salt, sodium chloride and dispersants, dusting agents and sequestrants, such as tetrasodium pyrophosphate.

The invention accordingly relates also to solid dye preparations for the dyeing of paper which comprise dyes of formula (1) or (2).

In recent years, the use of concentrated aqueous solutions of dyes has gained in importance, specifically because of the advantages which such solutions have over dyes in powder form. By using solutions, the difficulties associated with the formation of dust are avoided and the user is freed from the time-consuming and often difficult dissolution of the dye powder in water. The use of concentrated solutions has been prompted furthermore by the development of continuous dyeing processes for paper, since in those processes it is advantageous to add the solution directly to the hollander or at any other suitable point in the paper-making.

The invention therefore relates also to concentrated aqueous solutions of dyes of formula (1) or (2) which comprise, for example, from 1 to 50 percent by weight, especially from 5 to 40 percent by weight, and preferably from 8 to 30 percent by weight, dye, based on the total weight of the solution.

Concentrated aqueous solutions of dyes of formula (1) or (2) can be prepared, for example, by filtering the dye suspension obtained in the preparation of the dye, subjecting the filtrate, if desired, to desalination, for example by a membrane separation technique, and then stabilising it with an acid, for example formic acid, acetic acid or lactic acid, and by the addition of auxiliaries, such as urea, ε-caprolactam or polyethylene glycol.

The dye solutions so prepared preferably contain from 400 to 900 parts of water, from 0 to 400 parts of an organic carboxylic acid, for example formic acid, acetic acid, propionic acid or lactic acid, and from 0 to 200 parts of further additives, such as urea, ε-caprolactam or polyethylene glycol, per 100 parts of dye.

The aqueous concentrates according to the invention, which are stable at storage temperatures of up to −5° C., are suitable for the dyeing of paper, on which they produce attractive red shades.

The dyes of formula (1) or (2) can also be employed for the dyeing of textile materials of cellulose, for example cotton, and for the dyeing of leather and glass fibres.

The following Examples serve to illustrate the invention but do not limit the invention thereto. Parts and percentages relate to weight, unless otherwise indicated.

APPLICATION EXAMPLE 1

50 parts of chemically bleached beechwood sulfite pulp are mixed with 50 parts of bleached pinewood pulp RKN 15 (freeness 22° SR) and 0.2 part of the dye of formula

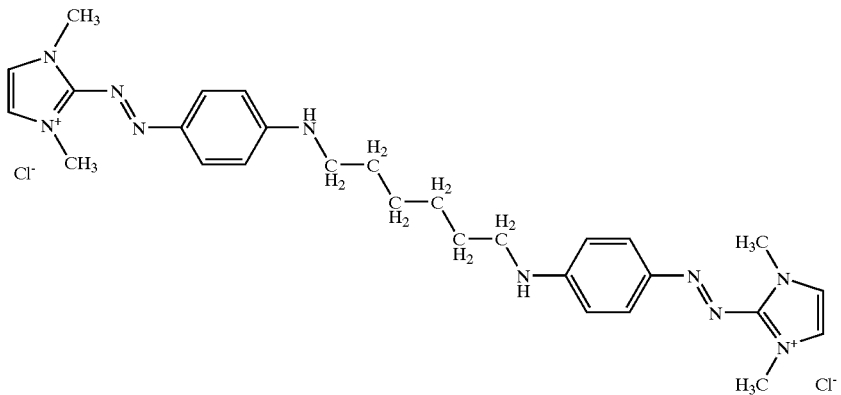

(101)

in water (pH 6, water hardness 10° dH [German hardness], temperature 20°, liquor ratio 1:40). After 15 minutes' stirring, sheets of paper are produced on a Frank sheet-former. The paper has been dyed red.

Similar results are obtained if 0.2 parts of the dye of formula (101) are replaced by the same amount of a dye of formula

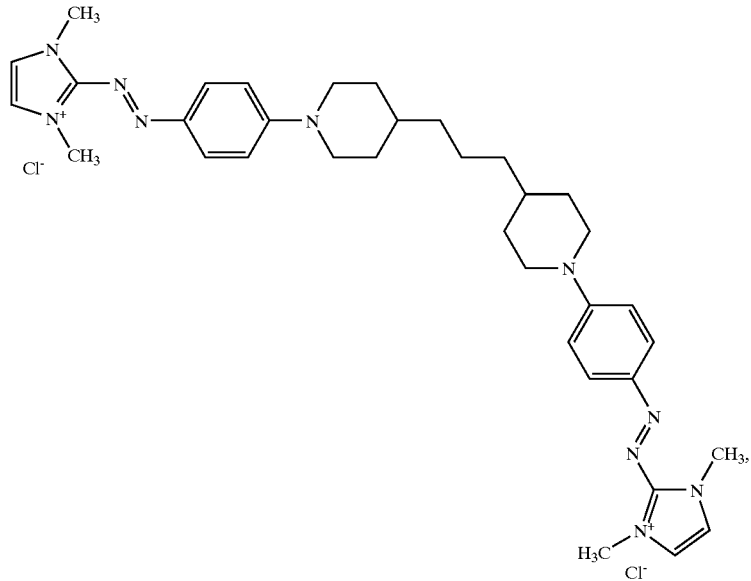

(102)

-continued

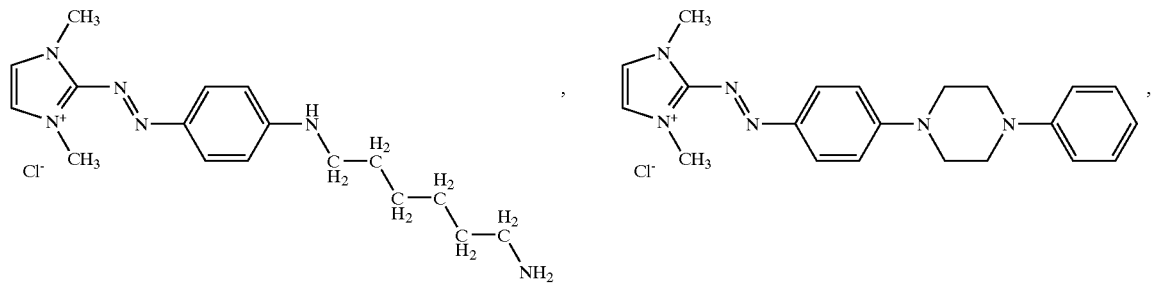

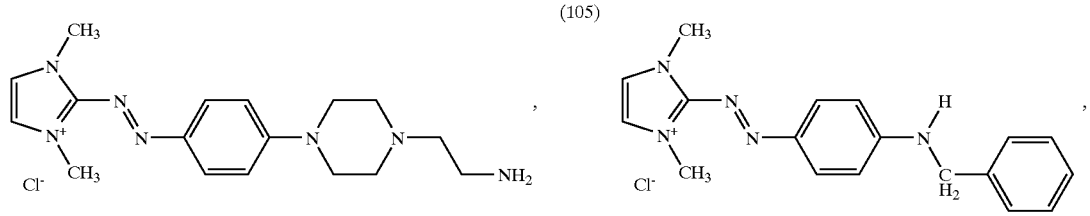

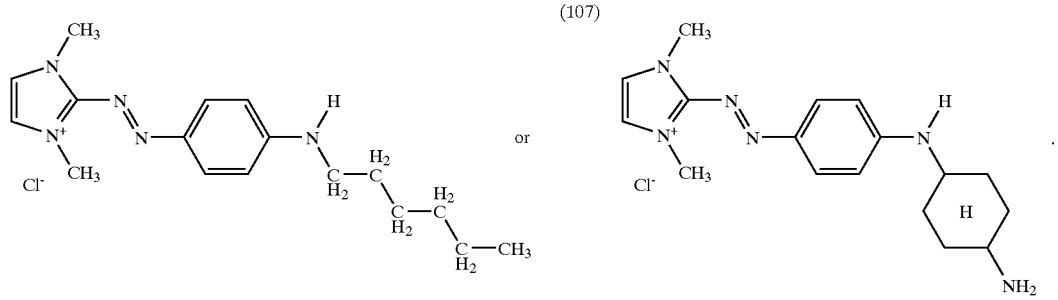

APPLICATION EXAMPLE 2

A paper web is produced from bleached beechwood sulfite pulp (22° SR) on a continuous laboratory papermaking machine. Ten seconds before the headbox, an aqueous solution of the dye of formula (101) according to Example 1 is metered continuously into the thin pulp with strong turbulence (0.3% strength dyeing, liquor ratio 1:400, water hardness 10° dH, pH 6, temperature 20°). A red dyeing is produced on the paper web.

Similar results are obtained if in Application Example 2 the dye of formula (101) is replaced by the dye formula (102), (103), (104), (105), (106), (107) or (108).

PREPARATION EXAMPLE 1

Dye:

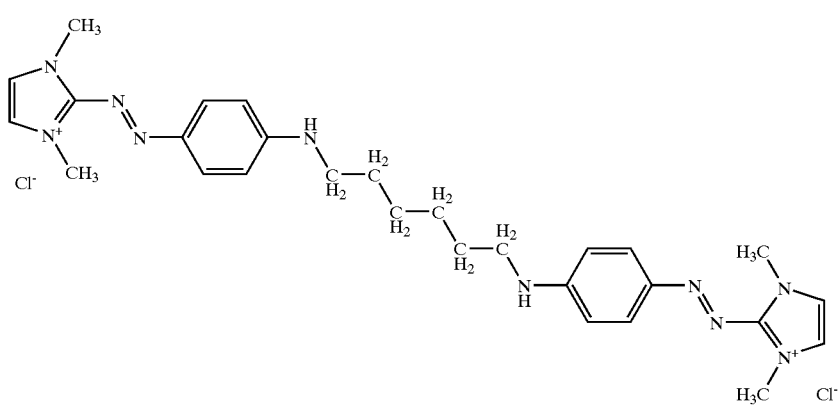

Educt:

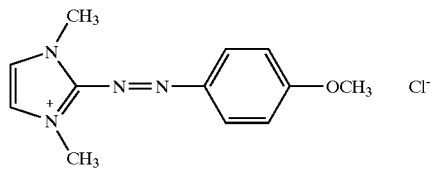

53.2 g of the educt of formula (109) is slurried in 36 g methanol at room temperature. The temperature is then raised to 45–50 ° C. and 10.3 g of 1,6-diamino-hexane is added. The mixture is stirred for 17 hours, the temperature is raised to 60° C. and hold for other 24 hours with stirring. Then the reaction mass is diluted with 140 g of methanol, cooled during 5 hours to room temperature, when crystallization occurs. The crystal suspension is separated by filtration, washed twice with 20 g methanol, then with 20 g 2-propanol and dried to yield 50 g of a dark powder.

PREPARATION EXAMPLE 2

(103)

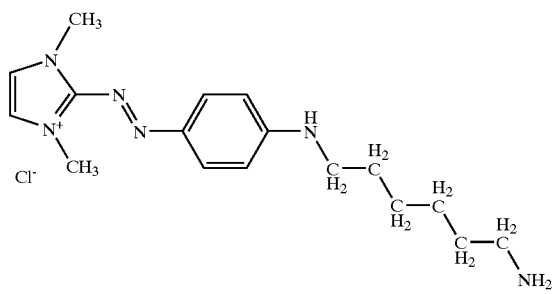

53.2 g of the educt of formula (109) is slurried in 560 g 2-propanol at room temperature. The temperature is then raised to 45–50° C. and 30 g of 1,6-diamino-hexane is added. The mixture is stirred for 18 hours. Then the reaction mass is cooled during 5 hours to room temperature, when crystallization occurs. The crystal suspension is separated by filtration. Then the reaction mass is concentrated by distillation of ca. 200 g 2-propanol and diluted with 100 g methyl-tertbutyl ether when the product crystallizes. The crystals are separated by filtration, washed twice with 20 g methyl-tertbutyl ether and dried to get 45 g of a dark powder.

PREPARATION EXAMPLE 3

(104)

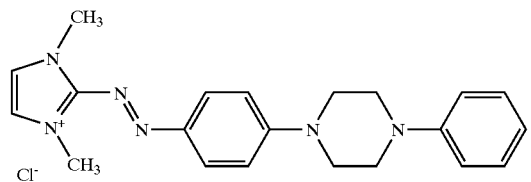

53.2 g of the educt of formula (109) is slurried in 40 g 2-propanol at room temperature. The temperature is then raised to 45–50° C. and 40 g of N-phenylpiperazine is added. The mixture is stirred for 30 hours. Then the reaction mass is diluted with 140 g of methyl-ethyl-ketone, cooled to room temperature, when crystallization occurs. The crystal suspension is separated by filtration, washed twice with 20 g methyl-ethyl-ketone and dried in a vacuum dryer to get 63 g of a dark powder.

PREPARATION EXAMPLE 4

(102)

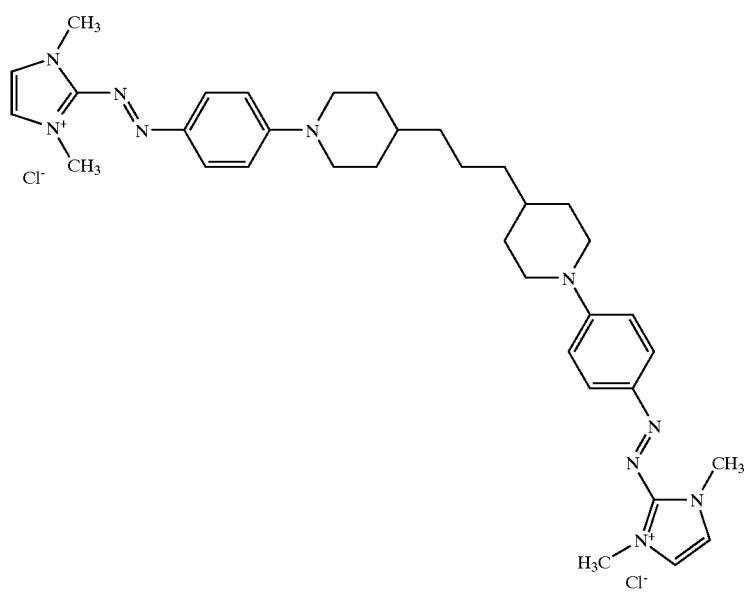

53.2 g of the educt of formula (109) is slurried in 26 g dimethyl-formamide and 36 g methanol at room temperature. The temperature is then raised to 45–50° C. and 20.5 g of dipiperidino-propane is added. The mixture is stirred for 17 hours; the temperature is raised to 60° C. and hold for other 24 hours with stirring. Then the reaction mass is diluted in 1–2 hours with 140 g of methanol, cooled during 5 hours to room temperature, when crystallization occurs. The crystal suspension is separated by filtration, washed twice with 20 g methanol, then with 20 g 2-propanol and dried in a vacuum dryer to get 60 g of a dark powder.

PREPARATION EXAMPLE 5

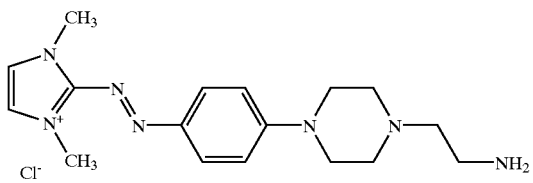

(105)

39 g of 2-aminoethyl-piperazin are solved in 100 g glycolic acid methyl ester. Traces of water are eliminated by vacuum distillation. Adding 0.2 g of sodium methoxide as catalyst, the reaction is carried out by refluxing and distilling of ca. 6 g of methanol. Then the excess of ester is distilled off under vacuum. The residual is the 2-piperazino-etylamide of glycolic acid that is further reacted with 60.6 g of the educt of formula (109) dissolved in 43 ml of 2-propanol. The temperature is then raised to 49–50° C. and the mixture is stirred for 30 hours.

Then the reaction mass is diluted with 140 g of methyl-ethylketone, cooled during 4 hours to room temperature, when crystallization occurs. The crystal suspension is separated by filtration, washed twice with 20 g methyl-ethylketone, then with 20 g 2-propanol and dried to get 86 g of a dark powder. The glycolic acid group is hydrolyzed in water and chlorhidric acid at 80° C. and recristallized from water. After drying there are obtained 76 g product of the given formula.

PREPARATION EXAMPLE 6

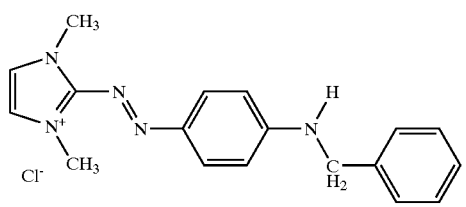

(106)

60.6 g of the educt of formula (109) is slurried in 43 g 2-propanol at room temperature. The temperature is then raised to 45–50° C. and 30.3 g of benzyl amine is added. The mixture is stirred for 20 hours for the completion of reaction. Then the reaction mass is diluted in 0.5 hours with 140 g of methyl-ethyl-ketone, cooled during 3 hours to room temperature, when crystallization occurs. The crystal suspension is separated by filtration, washed twice with 20 g methyl-ethyl-ketone, then with 20 g 2-propanol and dried under vacuum to get 53 g of a dark powder.

PREPARATION EXAMPLE 7

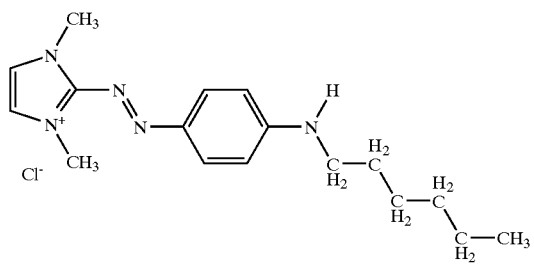

(107)

60 g of the educt of formula (109) is slurried in 45 g 2-propanol at room temperature. The temperature is then raised to 45–50° C. and 20 g of n-hexylamine is added. The mixture is stirred for 17 hours. Then the reaction mass is diluted with 140 g of methyl-ethylketone, cooled during 3 hours to room temperature, when crystallization occurs. The crystal suspension is separated by filtration, washed twice with 20 g methyl-ethylketone and dried at vacuum to get ca. 50 g of a dark powder.

PREPARATION EXAMPLE 8

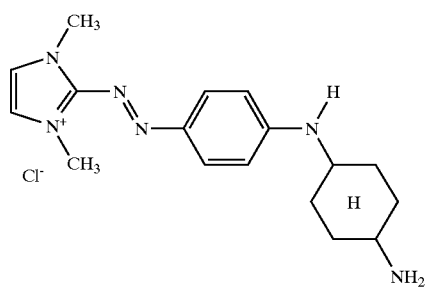

(108)

53.2 g of the educt of formula (109) is slurried in 460 g 2-propanol at room temperature. The temperature is then raised to 45–50° C. and 30 g of 1,4-diamino-cyclohexane is added. The mixture is stirred for 18 hours. Then the reaction mass is cooled during 3 hours to room temperature, when crystallization occurs. The suspension is separated by filtration. Then the suspension is concentrated by distillation of ca. 200 g 2-propanol and diluted with 200 g methyl-tertbutyl ether, when the product crystallizes. The crystals are separated by filtration, washed twice with 20 g methyl-tertbutyl ether and dried under vacuum to get 40 g of a dark powder.

What is claimed is:

1. A dye of formula

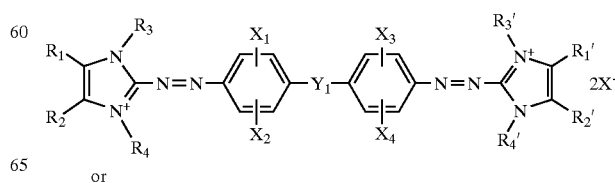

(1)

or

-continued

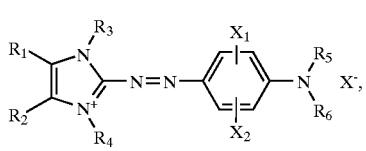
(2)

wherein
- $R_1$, $R_1'$, $R_2$ and $R_2'$ are each independently of the others hydrogen, $C_1$–$C_4$alkyl, halogen or nitro,
- $R_3$, $R_3'$, $R_4$ and $R_4'$ are each independently of the others $C_1$–$C_4$alkyl unsubstituted or substituted by OH, $C_1$–$C_4$alkoxy, halogen, CN or phenyl,
- $R_5$ is hydrogen or $C_1$–$C_4$alkyl,
- $R_6$ is unsubstituted $C_5$–$C_{12}$alkyl; or $C_5$–$C_8$cycloalkyl;
- $X_1$, $X_2$, $X_3$ and $X_4$ of the compound of formula (1) are each independently of the others hydrogen, $C_1$–$C_4$alkyl, $C_1$–$C_4$alkoxy or halogen, and
- $X_3$ and $X_4$ of the compound of formula (2) are each indecendently of the others hydrogen, $C_1$–$C_4$alkyl, $C_1$–$C_4$alkoxy or halogen, and
- $X_1$ and $X_2$ of compound of formula (2) are hydrogen, and
- $Y_1$ is a bridging member of formula

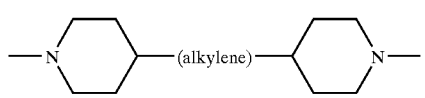

or —NH—$(CH_2)_6$—NH—, and $X^-$ is an anion.

2. A dye according to claim 1, wherein $R_1$, $R_1'$, $R_2$ and $R_2'$ are each methyl or hydrogen.

3. A dye according to claim 1, wherein $R_3$, $R_3'$, $R_4$ and $R_4'$ are each ethyl, hydroxyethyl or methyl.

4. A dye according to claim 1, wherein $X_1$, $X_2$, $X_3$ and $X_4$ of the compound of formula (1) and $X_3$ and $X_4$ of the compound of formula (2) are each methoxy, methyl, hydrogen or chlorine.

5. A dye according to claim 1, wherein $Y_1$ is a bridging member of formula

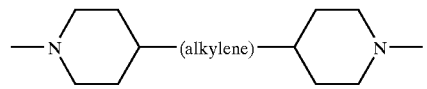

and alkylene is a straight-chain or branched $C_1$–$C_{12}$alkylene radical.

6. A dye according to claim 5, wherein alkylene is a straight-chain or branched $C_1$–$C_6$alkylene radical.

7. A dye according to claim 1, wherein $Y_1$ is a bridging member of formula —NH—$(CH_2)_6$—NH—.

8. A dye according to claim 1 of formula

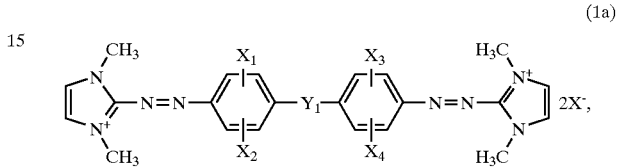
(1a)

wherein
- $X_1$, $X_2$, $X_3$ and $X_4$ are each independently of the others hydrogen, methyl or methoxy,
- $Y_1$ is a radical of formula —NH—$(CH_2)_6$—NH—, and
- $X^-$ is an anion.

9. A dye according to claim 1 of formula

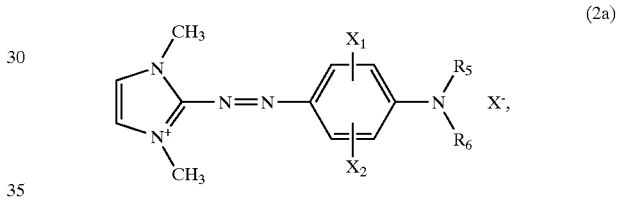
(2a)

wherein
- $X_1$ and $X_2$ are hydrogen, and
- $R_5$, $R_6$ and $X^-$ are as defined in claim 1.

10. A dye according to claim 1, wherein $R_5$ is hydrogen.

11. A dye according to claim 1, wherein
- $R_6$ is unsubstituted $C_5$–$C_{12}$alkyl; or amino-substituted $C_5$–$C_6$cycloalkyl.

12. A dye according to claim 1, wherein $X^-$ is a chloride, hydrogen sulfate, sulfate, methosulfate, phosphate, formate, lactate or acetate.

13. A dye according to claim 1, wherein $X^-$ is a chloride.

14. A method of dyeing or printing, leather, paper or glass fibres, which comprises contacting at least one of these with a dye of formula

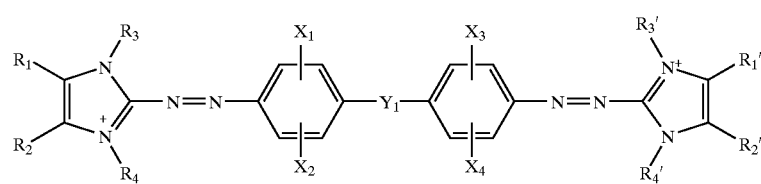
(1)

2X⁻ or

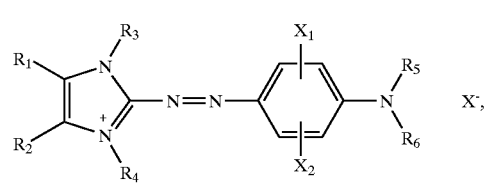
(2)

wherein

R$_1$, R$_1$', R$_2$ and R$_2$' are each independently of the others hydrogen, C$_1$–C$_4$alkyl, halogen or nitro, R$_3$, R$_3$', R$_4$ and R$_4$' are each independently of the others C$_1$–C$_4$alkyl unsubstituted or substituted by OH, C$_1$–C$_4$alkoxy, halogen, CN or phenyl, R$_5$ is hydrogen or C$_1$–C$_4$alkyl, R$_6$ is unsubstituted or amino-substituted C$_5$–C$_{12}$alkyl; or unsubstituted or amino-substituted C$_5$–C$_8$cycloalkyl; or phenyl-substituted C$_1$–C$_4$alkyl;

or wherein R$_5$ and R$_6$ together with the nitrogen atom linking them form a piperazine ring, which is substituted, at the nitrogen atom that is not bonded to the phenyl group, by C$_1$–C$_4$alkyl or phenyl, the alkyl and phenyl radicals mentioned as substituents of the nitrogen atom of the piperazine ring being unsubstituted or substituted by amino, X$_1$, X$_2$, X$_3$ and X$_4$ of the compound of formula (1) are each independently of the others hydrogen, C$_1$–C$_4$alkyl, C$_1$–C$_4$alkoxy or halogen, and X$_3$ and X$_4$ of the compound of formula (2) are each independently of the others hydrogen, C$_1$–C$_4$alkyl, C$_1$–C$_4$alkoxy or halogen, and X$_1$ and X$_2$ of the compound of formula (2) are hydrogen, Y$_1$ is a bridging member of formula

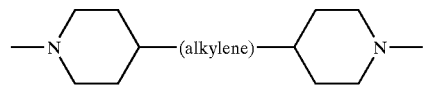

or —NH—(CH$_2$)$_6$—NH—, and

X$^-$ is an anion.

15. A method according to claim 14, wherein leather or paper is dyed or printed.

* * * * *